US012766064B2

(12) United States Patent
Bruno

(10) Patent No.: US 12,766,064 B2
(45) Date of Patent: Oct. 20, 2026

(54) MOBILITY ASSISTIVE DEVICE

(71) Applicant: John Douglas Bruno, Mount Laurel, NJ (US)

(72) Inventor: John Douglas Bruno, Mount Laurel, NJ (US)

( * ) Notice: Subject to any disclaimer, the term of this patent is extended or adjusted under 35 U.S.C. 154(b) by 0 days.

(21) Appl. No.: 19/349,255

(22) Filed: Oct. 3, 2025

(65) Prior Publication Data

US 2026/0026995 A1 Jan. 29, 2026

Related U.S. Application Data

(63) Continuation-in-part of application No. 18/607,204, filed on Mar. 15, 2024, now abandoned.

(60) Provisional application No. 63/490,704, filed on Mar. 16, 2023.

(51) Int. Cl.

| | |
|---|---|
| ***A61H 3/00*** | (2006.01) |
| ***A61F 5/01*** | (2006.01) |
| ***A61H 1/02*** | (2006.01) |

(52) U.S. Cl.

CPC .............. *A61H 3/00* (2013.01); *A61F 5/0113* (2013.01); *A61H 1/0262* (2013.01); *A61H 1/0266* (2013.01); *A61H 2003/007* (2013.01); *A61H 2201/1276* (2013.01); *A61H 2201/1614* (2013.01); *A61H 2201/1619* (2013.01); *A61H 2201/164* (2013.01); *A61H 2201/165* (2013.01); *A61H 2201/1652* (2013.01)

(58) Field of Classification Search

CPC .... A61F 5/0113; A61F 5/0102; A61F 5/0106; A61F 5/3715; A63B 21/0552; A63B 21/0557

See application file for complete search history.

(56) References Cited

U.S. PATENT DOCUMENTS

| | | | |
|---|---|---|---|
| 4,010,744 A | 3/1977 | Boyen | |
| 4,252,112 A | 2/1981 | Joyce | |
| 4,697,808 A | 10/1987 | Larson et al. | |
| 5,716,307 A | 2/1998 | Vadher | |
| 7,354,413 B2 | 4/2008 | Fisher | |
| 7,931,571 B2 | 4/2011 | Bernardoni | |
| 7,998,041 B1 * | 8/2011 | Johnson ............. | A63B 21/0552 482/124 |
| 9,452,076 B2 | 9/2016 | Hatzis et al. | |

(Continued)

FOREIGN PATENT DOCUMENTS

WO 2011070438 A1 6/2011

*Primary Examiner* — Kari K Rodriquez

(57) ABSTRACT

An assistive device that can be worn in normal daily activities that improves dorsiflexion in stance phase and correct hyperextension of the knee to help restore a functional gait pattern. The device includes an attachable foot stirrup strap, two long heavy duty elastic cords with hooks to attach to the foot stirrup strap and loops to attach to a shoulder strap, a thigh strap with clamp that allows for adjustment of tension to overcome foot drop and promote knee flexion in the proper direction by providing a point for the elastic cords to cross without entangling. Further, the shoulder strap includes a shoulder pad for comfort and a buckle that allows for adjustment of tension. Furthermore, the foot stirrup strap may be detachably connected to a foot/shoe of the user with the help of elastic connectors or permanently attached to the shoe with the help of an adhesive.

13 Claims, 7 Drawing Sheets

(56) References Cited

U.S. PATENT DOCUMENTS

| | | | |
|---|---|---|---|
| 10,390,973 B2 | 8/2019 | Tong et al. | |
| 11,331,529 B1 * | 5/2022 | Cranke .............. | A63B 21/4021 |
| 2017/0105862 A1 | 4/2017 | Griggs | |
| 2017/0105864 A1 | 4/2017 | Muccio | |
| 2019/0343670 A1 | 11/2019 | Ruprecht et al. | |

* cited by examiner

MOBILITY ASSISTIVE DEVICE

FIELD OF THE INVENTION

The present invention relates generally to mobility assistive devices. More specifically, the present invention relates to wearable devices to improve dorsiflexion and thereby improve gait by preventing foot drop and assisting in knee and hip flexion.

BACKGROUND OF THE INVENTION

Several medical conditions such as multiple sclerosis or stroke can lead to weakness of the lower extremities resulting in foot drop, reduced knee flexion, exaggerated hip circumduction and hip hiking during the swing phase of the gait cycle. Assistance during gait training is necessary to properly align the trunk and guide the leg through normal gait trajectory.

A common technique utilized by physical therapists to improve gait during a rehabilitation session is the use of an elastic band. In this technique the band is-cris-crossed around the foot near the toe, and then cris-crossed again behind the leg but above the knee, and then cris-crossed again around the waist. This technique helps pick up the foot to prevent dragging of the toe, helps initiate knee flexion to overcome knee locking, and provides some help in hip flexion. However, tying the band to provide the necessary support at the necessary joints requires visiting the clinic and/or professional assistance.

An objective of the present invention is to provide a device that can be worn full-time, outside the clinic, and can provide identical directional forces obtained by the elastic band technique in a much more robust and durable form. It is a further objective of the present invention to direct the forces necessary for hip and knee flexion to a padded shoulder strap that can be adjusted to vary the force applied. It is a further objective of the present invention to provide a thigh strap that allows for the elastic cords attached to both sides of the foot to be cris-crossed behind the leg and above the knee, and locked into place with an adjustable clamp to adjust the tension for foot drop, knee flexion and allow for correction of any toe-in or toe-out abnormalities. It is a further objective of the present invention to provide a foot stirrup strap that can be held in place by elastic bands or glued in place, that allows for easy attachment of elastic cords and is made of durable abrasion resistant strapping.

SUMMARY OF THE INVENTION

The present invention comprises an assistive device that can be worn in normal daily activities, can improve dorsiflexion in stance phase and correct hyperextension of the knee to help restore a functional gait pattern. To accomplish this, the device includes an attachable foot stirrup strap, two long heavy duty elastic cords with hooks to attach to foot stirrup and loops to attach to shoulder strap, a thigh brace with clamp that allows for adjustment of tension to overcome foot drop and promote knee flexion in the proper direction by providing a point for the elastic cords to cross, and a shoulder strap with a shoulder pad for comfort and a buckle that allows for adjustment of tension.

DETAILED DESCRIPTION OF THE INVENTION

Figure 1:
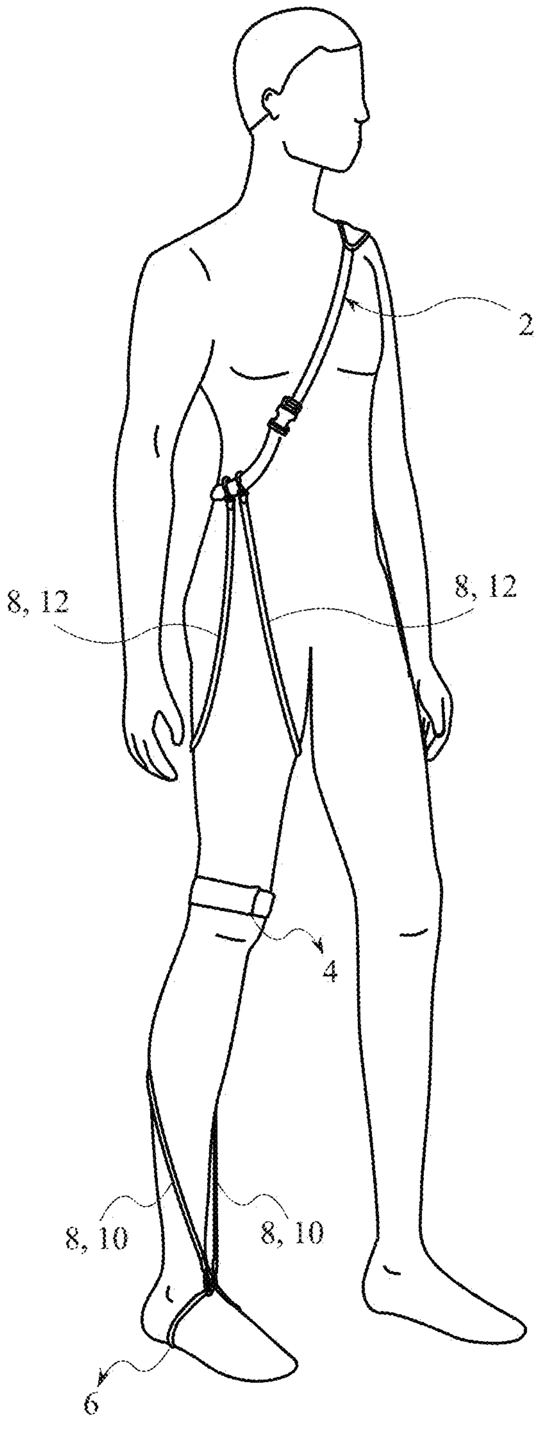
FIG. 1 is a top-front-left perspective view of a user wearing a preferred embodiment of the present invention.
Figure 2:
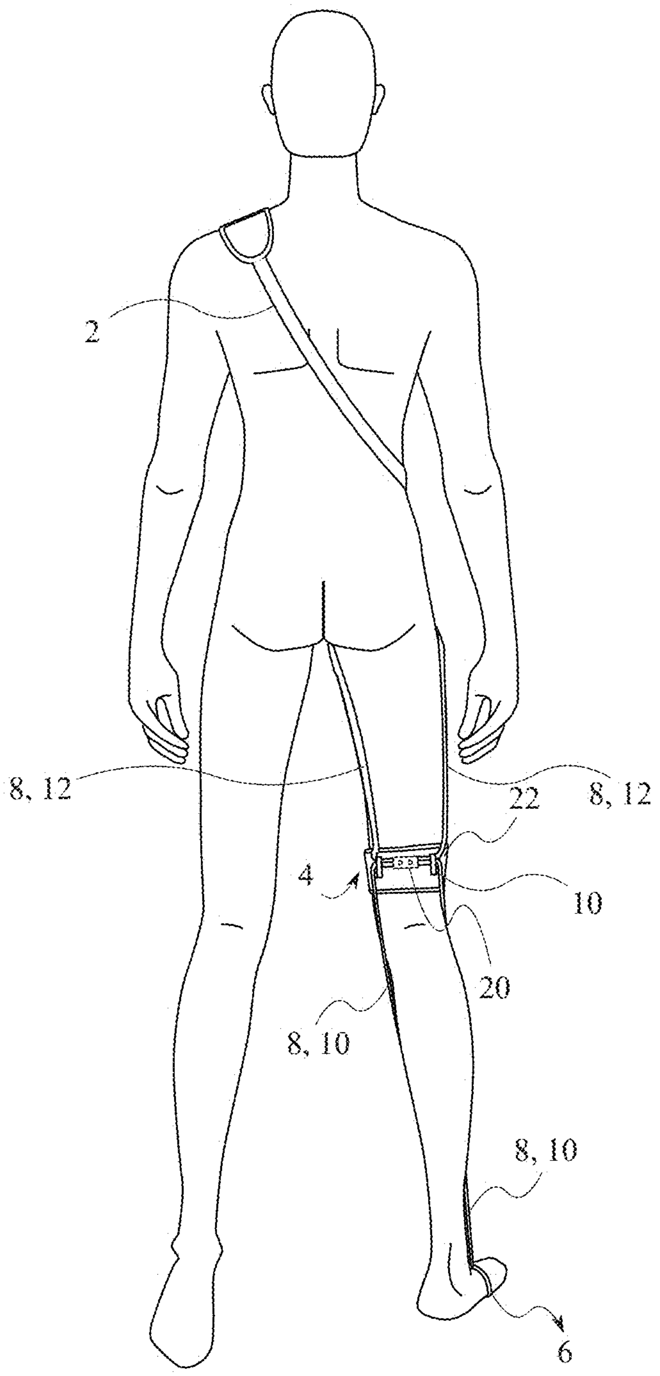
FIG. 2 is a rear elevational view of the user wearing the present invention.

All illustrations of the drawings are for the purpose of describing selected versions of the present invention and are not intended to limit the scope of the present invention.

The present invention provides an assistive device that directs forces around three critical points: the front of the foot, the back of the thigh and the shoulder. The assistive device lifts the front of the foot towards the back of the thigh and provides a force to initiate knee flexion. The assistive device redirects the tension in the device around the back of the knee and upward towards the shoulder. The shoulder provides a lifting force to the device. The tension between the shoulder and the knee helps lift the thigh while walking. As the wearer walks, the lifting force on the foot lifts the foot with minimal or no muscular force from the wearer.

In reference to FIG. 1 through FIG. 7, the present invention is a mobility assistive device.

According to a preferred embodiment, the present invention comprises a torso strap 2, a thigh strap 4, a foot stirrup strap 6, and a plurality of elastic cords 8. The torso strap 2 is a main support device that is worn across the torso of a user. The torso strap 2 transfers the tensional force from the plurality of elastic cords 8 to the shoulder of the wearer, thereby providing some help in lifting the leg. The torso strap 2 includes a shoulder pad and a buckle. The shoulder pad provides a cushion to enhance comfort for the wearer. The buckle provides an easier mechanism for donning and doffing the assistive device. The buckle includes a length adjustment mechanism that allows the wearer to adjust the length of the torso strap. Adjusting the length may enhance wearer comfort and allows the wearer to adjust the tension in the elastic cords, thereby increasing or decreasing the lifting force on the foot and/or thigh. For example, the wearer may use the torso strap 2 to make on-the-go adjustments to the tension in the elastic cords 8.

The thigh strap 4 is another supporting component of the present invention that goes around the thigh of the user. The thigh strap 4 includes a leg strap fastener that allows the wearer to adjust the length of the thigh strap. Preferably, the fastener is a hook and loop fastener. Thus, in other words, the thigh strap 4 encircles the thigh of the wearer, and the thigh strap 4 fastener allows the wearer to adjust the length of the thigh strap for proper position and tightness.

The foot stirrup strap 6 is the third main component of the present invention that goes around the foot of the user. The plurality of elastic cords 8 provides the tensional lift needed for mobility assistance by connecting the torso strap 2 and the foot stirrup strap 6 to the thigh strap 4. More specifically, the plurality of elastic cords 8 provides a tensional force between the foot and the back of the knee and a tensional force between the back of the knee and the torso strap. The tensional force between the foot and the back of the knee lifts the foot while the wearer is walking and helps initiate knee flexion during the swing phase. The torso strap 2 transfers the tensional force from the elastic cords to the shoulder of the wearer also providing some help in lifting the leg. To that end, the plurality of elastic cords 8 comprises a first set of cords 10 and a second set of cords 12. Preferably, the first set of cords 10 is connected between the foot stirrup strap 6 and the thigh strap 4. Further, the second set of cords 12 is connected between the thigh strap 4 and the torso strap 2. To enable connectivity between the various straps, each of the plurality of clastic cords 8 has a loop positioned at the terminal ends of the elastic cord. The loop may be hooked onto different kinds of fasteners mounted on the torso strap 2 as well as the foot stirrup device. It should be noted that the torso strap 2, the thigh strap 4, the foot stirrup strap 6 and the plurality of elastic cords 8 may comprise any material, dimension, components, arrangement of components, etc. that are known to one of ordinary skill in the art, as long as the intents of the present invention are not altered.

Figure 4:
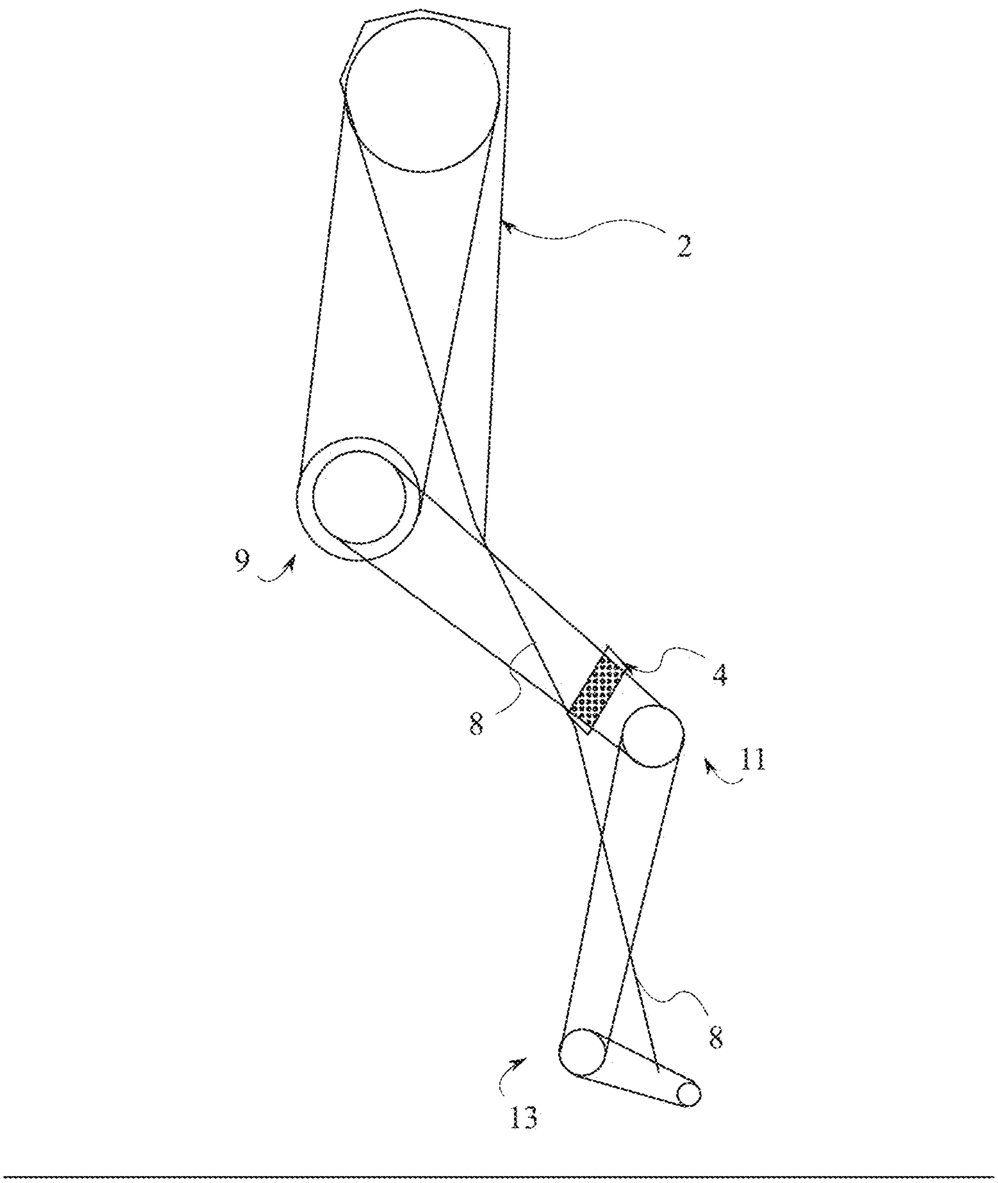
FIG. 4 is a schematic representation of main joints of a human body that is wearing the present invention, wherein a mid-swing phase of a human gait trajectory is represented.
Figure 5:
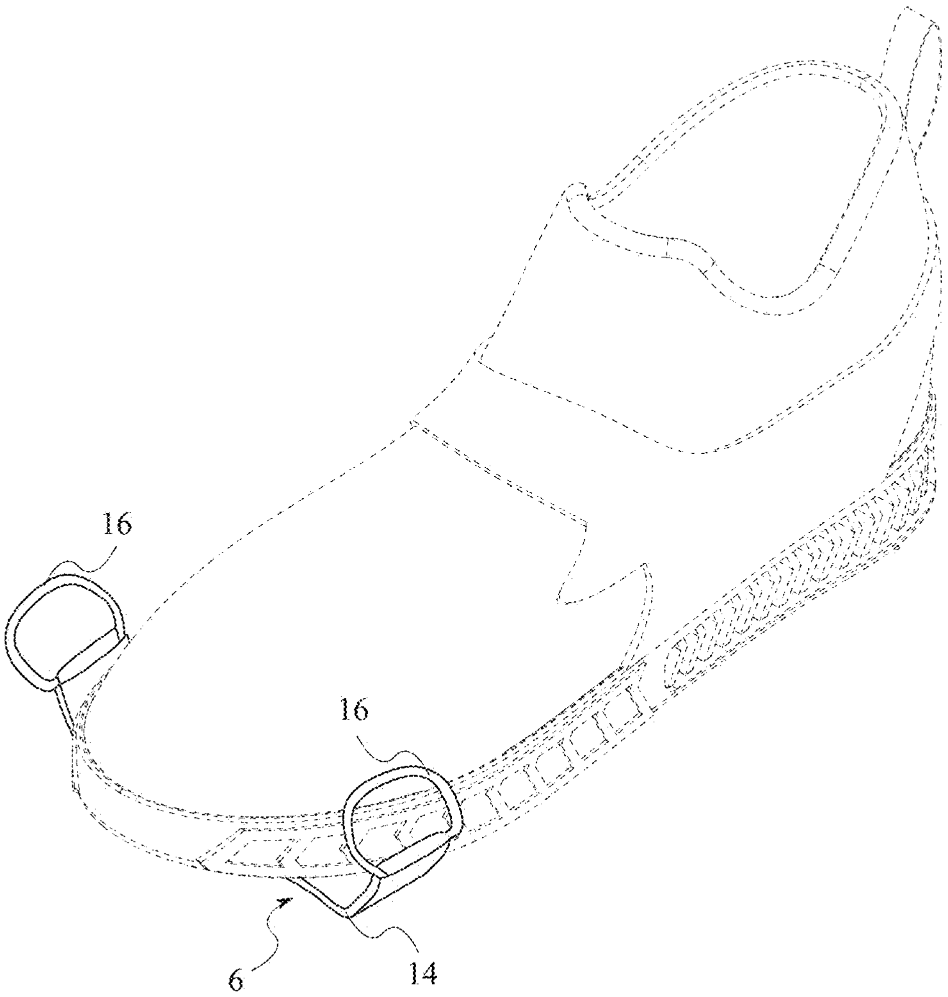
FIG. 5 is a top-front perspective view of a shoe, wherein a foot stirrup strap is permanently mounted onto a base of the shoe.
Figure 6:
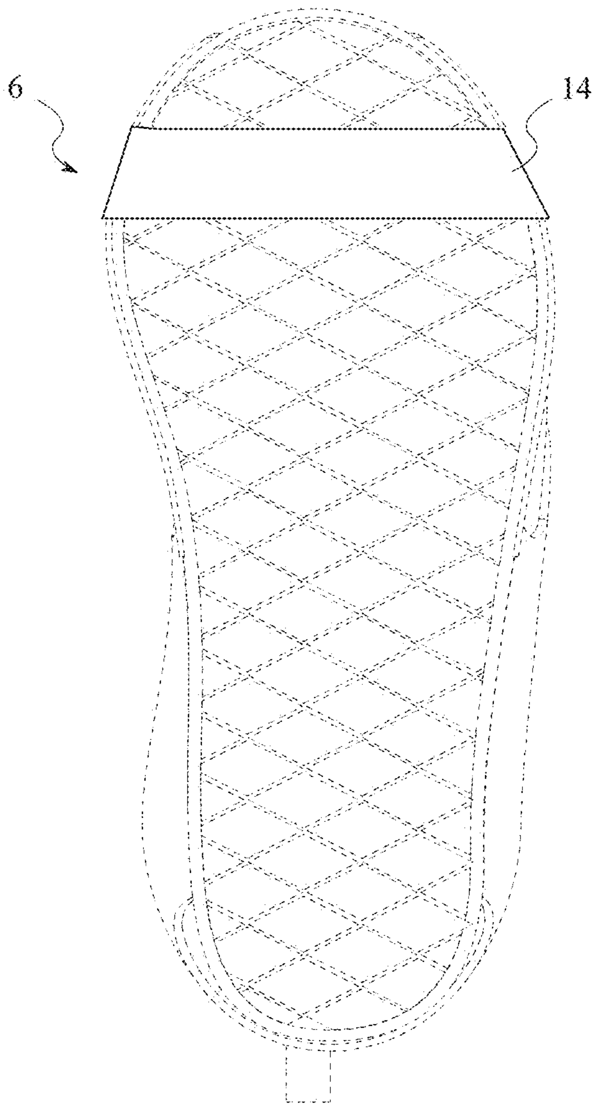
FIG. 6 is a rear elevational view of the shoe with the foot stirrup strap attached.

As seen in FIG. 4, and FIG. 5, the orientation and positioning of the various straps and elastic cords of the present invention create strong rotational forces in the right directions for the main three joints, (i.e., hip 9, knee 11, and ankle 13) that is required for an ideal human gait.

A more detailed description of the present invention follows.

According to the preferred embodiment, the foot stirrup strap 6 comprises a base support strap 14 and a plurality of fasteners 16. Preferably, the base support strap 14 is the strap that goes along the base of the foot of a user. Further, in the preferred embodiment, the base support strap 14 goes along the bottom surface of a user's shoe. To that end, the base support strap 14 is made of an abrasive resistant material for enabling seamless walking and a durable device. Further, the base support strap 14 is rectangular in shape. However, the base support strap 14 may be made of any other material and may comprise of any other shape, as long as the objectives of the present invention are fulfilled.

Continuing with the preferred embodiment, the plurality of fasteners 16 is terminally connected to opposing ends of the base support strap 14. The plurality of fasteners 16 helps connect the foot stirrup strap 6 with the plurality of elastic cords 8. To that end, each of the first set of cords 10 is connected to a corresponding fastener, wherein the corresponding fastener is from the plurality of fasteners 16. Preferably, the foot stirrup strap 6 is connected to a distal end of the first set of cords 10, and the thigh strap 4 is connected to a proximal end of the first set of cords 10.

Figure 7:
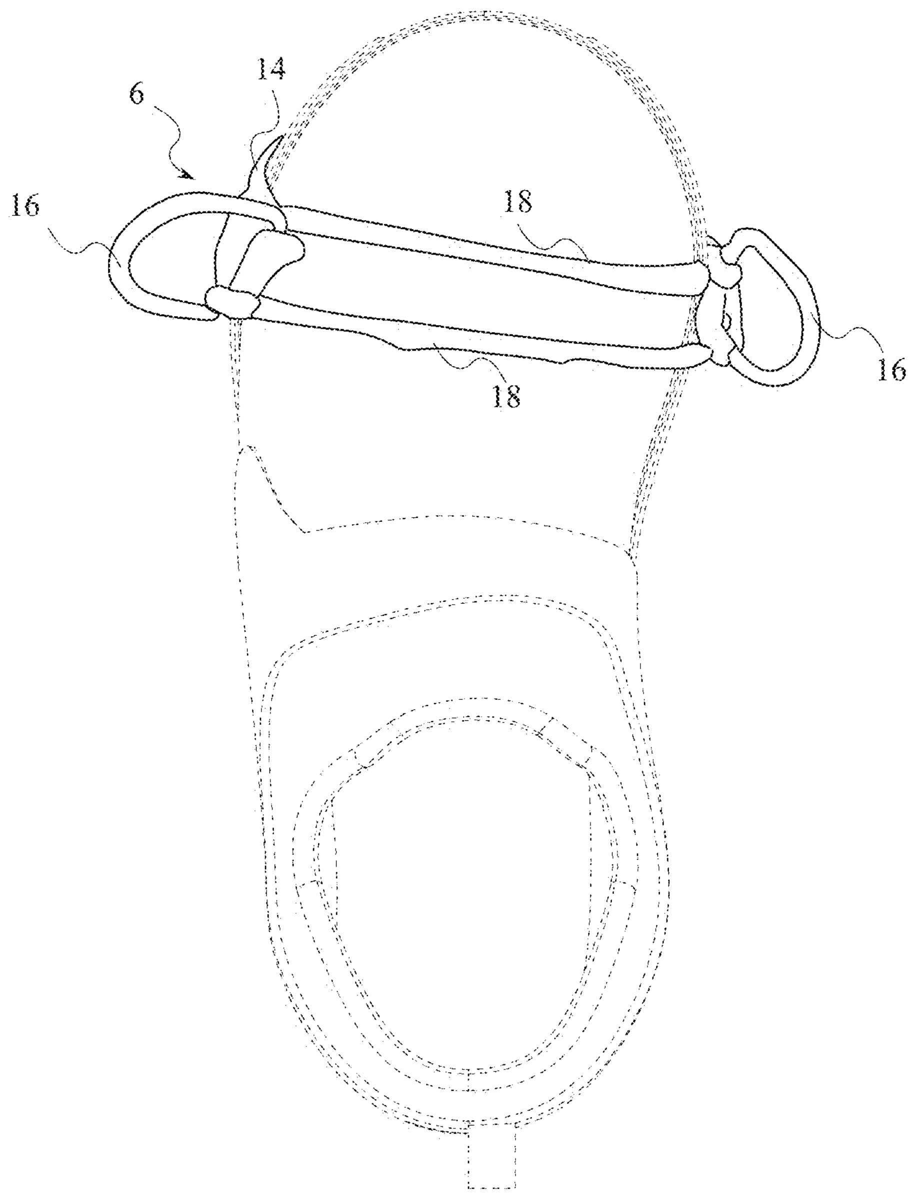
FIG. 7 is a top plan view of a shoe, wherein a foot stirrup strap with an elastic connector is temporarily mounted around the shoe.

As seen in FIG. 5 and FIG. 7, the plurality of fasteners 16 is D-rings. However, the plurality of fasteners 16 may include any other fastener or fastening technique that is known to one of ordinary skill in the art, as long as the intents of the present invention are not altered.

In reference to FIG. 7, the foot stirrup strap 6 comprises at least one elastic connector 18, wherein the at least one elastic connector 18 is connected between opposing edges of the base support strap 14. Thus, in one embodiment, wherein at least one elastic connector 18 connects the two ends of the base support strap 14, the foot stirrup strap 6 is detachably mounted around a shoe or foot of the user.

In another embodiment, and as seen in FIG. 5, the base support strap 14 is permanently attached to a shoe base. In this embodiment, the base support strap 14 is attached to the base of a shoe with the help of an adhesive. However, any other means of attachment may be used, as long as the intents of the present invention are not altered.

Figure 3:
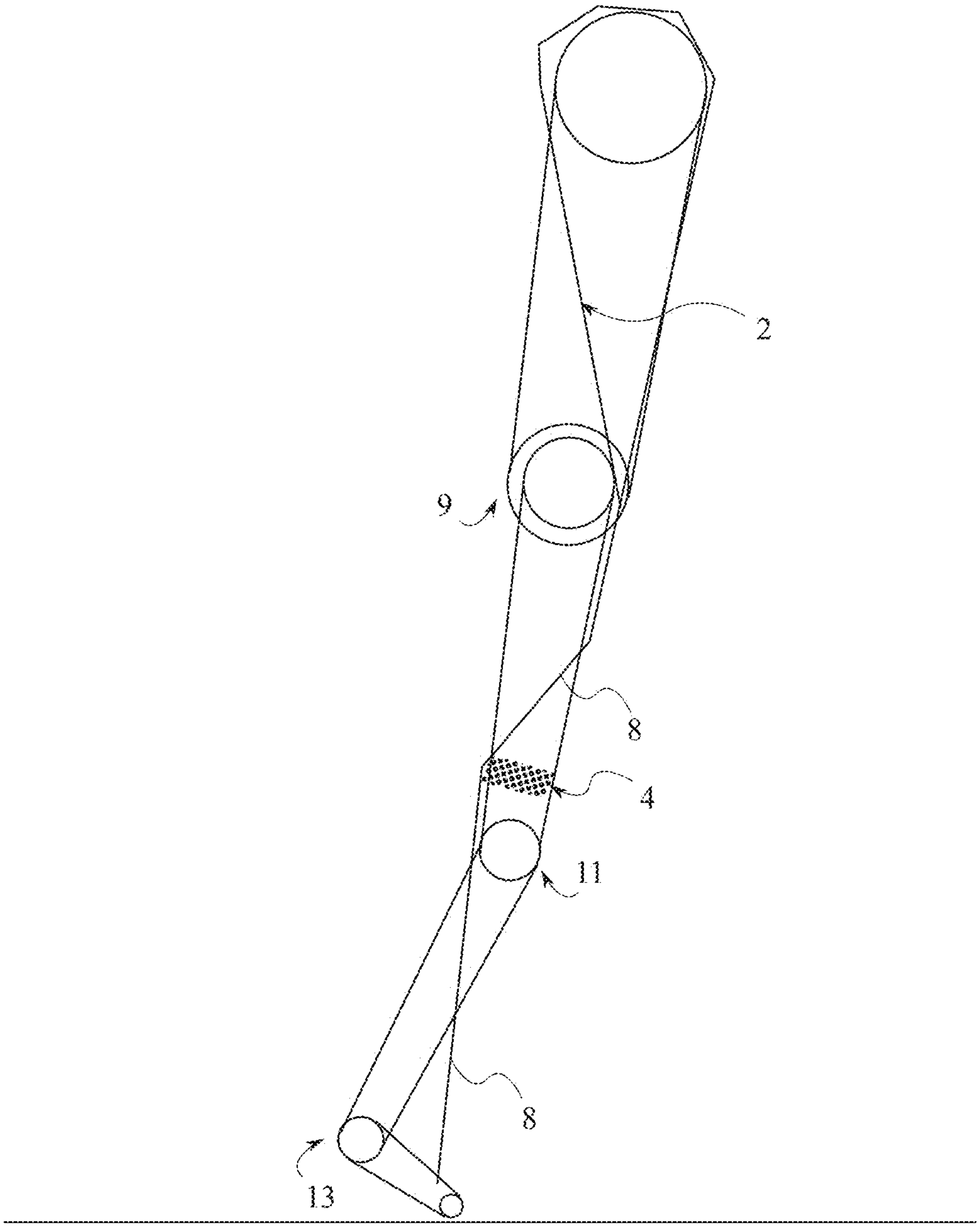
FIG. 3 is a schematic representation of main joints of a human body that is wearing the present invention, wherein a pre-swing phase of a human gait trajectory is represented.

As seen in FIG. 3, the leg strap 4 further comprising a clamp 20 and a strap body 22. The clamp 20 secures the plurality of elastic cords 8, preventing the elastic cords from moving relative to one another. In the preferred embodiment, the clamp 20 is closed with screws. The screws may be loosened to adjust the elastic cords 8, and the screws may be tightened to secure the elastic cords 8. For example, the wearer may use the clamp 20 to adjust the elastic cords before donning the assistive device. The thigh strap 4 secures the elastic cords 8 to prevent the elastic cords 8 from shifting around the leg during use. The thigh strap 4 provides an anchor point to redirect the tensional forces of the elastic cords 8. The position and tightness of the leg strap 4 can be adjusted to adjust the tension in the elastic cords. The thigh-strap 4 helps maintain the proper distribution of tensional forces in the elastic cords to aid the wearer when walking. Thus, the clamp 20 is centrally mounted along a length of the strap body 22, and the plurality of elastic cords 8 is secured within the clamp 20. Further, the first set of cords 10 and the second set of cords 12 are threaded through the clamp 20 without intersecting with each other.

To use the present invention, the foot stirrup strap 6 is attached to the shoe or foot of the wearer first. Next, the thigh leg strap 4 is strapped on the wearer's thigh, just above the knee. The elastic cords 8 are adjusted to achieve the desired tension. The clamp 20 is tightened to lock the elastic cords in place relative to each other. This adjustment of the elastic cords and clamp 20 is used to make coarse adjustments to the elastic cords. The torso strap 2 is then placed around the torso of the wearer. The length and position of the torso strap 2 is adjusted to make fine adjustments to the elastic cords.

Although the invention has been explained in relation to its preferred embodiment, it is to be understood that many other possible modifications and variations can be made without departing from the spirit and scope of the invention as hereinafter claimed.

What is claimed is:

1. A mobility assistive device comprising:

a torso strap;

a thigh strap;

a foot stirrup strap;

a plurality of elastic cords;

the plurality of elastic cords comprising a first set of cords and a second set of cords;

the first set of cords being connected between the foot stirrup strap and the thigh strap; and the second set of cords being connected between the thigh strap and the torso strap wherein the first set of cords and the second set of cords are routed rearwardly through a clamp mounted on a rearward position of the thigh strap;

wherein the first set of cords is configured to provide a tensional force behind a knee of a user;

and wherein the second set of cords provides an upward force on the thigh strap towards the torso strap.

2. The mobility assistive device of claim 1 further comprising:

the foot stirrup strap comprising a base support strap and a plurality of fasteners; and the plurality of fasteners being terminally connected to opposing ends of the base support strap.

3. The mobility assistive device of claim 2, wherein the plurality of fasteners is D-rings.

4. The mobility assistive device of claim 2, wherein the base support strap is made of an abrasive resistant material.

5. The mobility assistive device of claim 2 further comprising:

the foot stirrup strap comprising a at least one elastic connector; and the at least one elastic connector being connected between opposing ends of the base support strap.

6. The mobility assistive device of claim 2, wherein the base support strap is rectangular in shape.

7. The mobility assistive device of claim 2, wherein the base support strap is permanently attached to a shoe base.

8. The mobility assistive device of claim 2, wherein the foot stirrup strap is detachably mounted around a shoe.

9. The mobility assistive device of claim 2, wherein each of the first set of cords is connected to a corresponding fastener, wherein the corresponding fastener is from the plurality of fasteners.

10. The mobility assistive device of claim 1, wherein the foot stirrup strap is connected to a distal end of the first set of cords.

11. The mobility assistive device of claim 1, wherein the thigh strap is connected to a proximal end of the first set of cords.

12. The mobility assistive device of claim 1 further comprising:

the thigh strap further comprising a strap body; and the clamp being centrally mounted along a length of the strap body.

13. The mobility assistive device of claim 12, wherein the first set of cords and the second set of cords are threaded through the clamp without intersecting each other.

* * * * *